(12) United States Patent
Graf et al.

(10) Patent No.: US 6,235,917 B1
(45) Date of Patent: *May 22, 2001

(54) DINUCLEAR COMPLEXES AND POLYMERIZATION CATALYSTS THEREFROM

(75) Inventors: David D. Graf; Jerzy Klosin; Peter N. Nickias; Jasson T. Patton, all of Midland, MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/234,192

(22) Filed: Jan. 20, 1999

Related U.S. Application Data

(63) Continuation-in-part of application No. 09/141,659, filed on Aug. 28, 1998, now Pat. No. 6,153,776.

(51) Int. Cl.[7] .............. C07F 17/00; C07F 7/00; B01J 31/00
(52) U.S. Cl. .............. 556/11; 556/1; 556/12; 556/43; 556/53; 556/54; 556/58; 534/15; 502/103; 502/117; 526/160; 526/943
(58) Field of Search ............... 556/11, 12, 1, 556/43, 53, 54, 58; 534/15; 502/103, 117; 526/160, 943

(56) References Cited

U.S. PATENT DOCUMENTS

| | | | |
|---|---|---|---|
| 3,242,099 | 3/1966 | Manyik et al. | 252/429 |
| 5,055,438 | 10/1991 | Canich | 502/117 |
| 5,057,475 | 10/1991 | Canich et al. | 502/104 |
| 5,064,802 | 11/1991 | Stevens et al. | 502/155 |
| 5,096,867 | 3/1992 | Canich | 502/103 |
| 5,198,401 | 3/1993 | Turner et al. | 502/155 |
| 5,372,980 | * 12/1994 | Davis | 502/103 |
| 5,374,696 | 12/1994 | Rosen et al. | 526/126 |
| 5,470,993 | 11/1995 | Devore et al. | 556/11 |
| 5,585,508 | * 12/1996 | Kuber et al. | 556/11 |
| 5,627,117 | * 5/1997 | Mukaiyama et al. | 502/113 |
| 5,892,079 | * 4/1999 | Wilson, Jr. | 556/11 |
| 5,962,359 | * 10/1999 | Aulbach et al. | 502/103 |
| 6,010,974 | * 1/2000 | Kim et al. | 502/152 |

FOREIGN PATENT DOCUMENTS

| | | |
|---|---|---|
| 416815 | 7/1990 | (EP) . |
| 0739897 | 10/1996 | (EP) . |
| 0779295 | 6/1997 | (EP) . |

OTHER PUBLICATIONS

Chemical Abstract, vol. 120, No. 3, Jan. 17, 1994, Abstract No. 30861v. Elschenbroich, et al.
J. Organomet. Chem., R. Mulhaupt, et al., 460, 191, (1993).

* cited by examiner

Primary Examiner—Porfirio Nazario-Gonzalez

(57) ABSTRACT

Group 3–6 or Lanthanide metal complexes possessing two metal centers joined by means of a divalent bridging group joining trivalent moieties comprising boron or a member of Group 14 of the Periodic Table of the Elements, and optionally also comprising nitrogen, phosphorus, sulfur or oxygen, in the complexes, catalysts derived therefrom by combining the same with strong Lewis acids, Bronsted acid salts, salts containing a cationic oxidizing agent or subjected to bulk electrolysis in the presence of compatible, inert non-coordinating anions and the use of such catalysts for polymerizing olefins, diolefins and/or acetylenically unsaturated monomers are disclosed.

7 Claims, No Drawings

DINUCLEAR COMPLEXES AND POLYMERIZATION CATALYSTS THEREFROM

CROSS REFERENCE TO RELATED APPLICATION

This is a continuation in part of pending U.S. application Ser. No. 09/141,659, filed Aug. 28, 1998, the teachings of which are here in incorporated by reference.

BACKGROUND OF THE INVENTION

This invention relates to certain Group 3, 4 or Lanthanide metal complexes possessing two metal centers and to polymerization catalysts obtained therefrom. In one form this invention relates to such metal complexes per se. In another embodiment of the claimed invention, the complexes can be activated to form catalysts for the polymerization of olefins. Also included in the invention are processes for preparing such complexes and methods of using the catalysts in addition polymerizations.

Biscyclopentadienyl Group 4 transition metal complexes in which the metal is in the +4, +3 or +2 formal oxidation state, and olefin polymerization catalysts formed from such by combination with an activating agent, for example, alumoxane or ammonium borate, are well known in the art. Thus, U.S. Pat. No. 3,242,099 describes the formation of olefin polymerization catalysts by the combination of bis-cyclopentadienyl metal dihalides with alumoxane. U.S. Pat. No. 5,198,401 discloses tetravalent biscyclopentadienyl Group 4 transition metal complexes and olefin polymerization catalysts obtained by converting such complexes into cationic forms in combination with a non-coordinating anion. Particularly preferred catalysts are obtained by the combination of ammonium borate salts with the biscyclopentadienyl titanium, zirconium or hafnium complexes. Among the many suitable complexes disclosed are bis(cyclopentadienyl)zirconium complexes containing a diene ligand attached to the transition metal through σ-bonds where the transition metal is in its highest formal oxidation state. R. Mülhaupt, et al., *J. Organomet. Chem.*, 460,191 (1993), reported on the use of certain binuclear zirconocene derivatives of dicyclopentadienyl-1,4-benzene as catalysts for propylene polymerization.

Constrained geometry metal complexes, including titanium complexes, and methods for their preparation are disclosed in U.S. application Ser. No. 545,403, filed Jul. 3,1990 (EP-A-416,815); U.S. Pat. Nos. 5,064,802, 5,374,696, 5,055,438, 5,057,475, 5,096,867, and 5,470,993.

Metal complexes of the constrained geometry type containing two metal centers joined by means of a dianionic ligand separate from and unconnected to the ligand groups in such complexes that contain delocalized π-electrons, are previously taught, but not exemplified, in U.S. Pat. No. 5,055,438.

SUMMARY OF THE INVENTION

The present invention relates to dinuclear metal complexes corresponding to the formula:

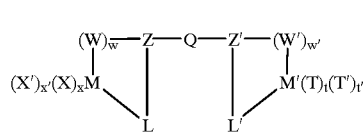

(I)

wherein:

M and M' are independently Group 3, 4, 5, 6, or Lanthanide metals;

L, L', W, and W', independently, are divalent groups having up to 50 nonhydrogen atoms and containing an aromatic π-system through which the group is bound to M, said L and W also being bound to Z, and said L' and W' also being bound to Z';

Z and Z' independently are trivalent moieties comprising boron or a member of Group 14 of the Periodic Table of the Elements, and optionally also comprising nitrogen, phosphorus, sulfur or oxygen, said Z and Z' having up to 20 atoms not counting hydrogen;

X and T independently each occurrence are anionic ligand groups having up to 40 atoms exclusive of the class of ligands containing an aromatic π-system through which the group is bound to M or M', or optionally two X groups or two T groups together form a $C_{4-40}$ conjugated or nonconjugated diene optionally substituted with one or more hydrocarbyl, silyl, halocarbyl, or halohydrocarbyl groups;

X' and T' independently each occurrence are neutral ligating compound having up to 20 atoms other than neutral diene compounds;

Q is a divalent anionic ligand group bound to both Z and Z', said Q having up to 20 nonhydrogen atoms;

w and w' are independently 0 or 1;

x and t are independently integers from 0 to 3, selected to provide charge balance; and x' and t' are independently numbers from 0 to 3.

Additionally according to the present invention there is provided a composition of matter useful as an addition polymerization catalyst comprising:

1) at least one dinuclear metal complex (I) as previously disclosed, and 2) one or more activating cocatalysts, the molar ratio of 1) to 2) being from 1:10,000 to 100:1, or the reaction product formed by converting 1) to an active catalyst by use of an activating technique.

Further additionally according to the present invention there is provided a process for polymerization of one or more addition polymerizable monomers comprising contacting said monomer or a mixture of said monomers with a catalyst comprising the aforementioned composition of matter.

The invented catalyst compositions allow the preparation of mixtures of polymers from a single monomer or mixture of monomers thereby forming directly a polymer blend in the reactor. This result is accentuated where different metals, different metal valencies or different ligand groups attached to the two metal centers are employed. Alternatively, the invention allows for increased incorporation of long chain branching in a polymer formed from a single monomer, especially ethylene, or a mixture of monomers, due to selection of one metal center adapted to forming oligomeric products terminated by vinyl functionality in combination with a second metal center adapted to form high molecular weight polymers or adapted to long chain α-olefin incorporation into a polymer.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

In all of the forgoing and succeeding embodiments of the invention, desirably, when w and w' are both 1, two X and two T groups together are a diene or substituted diene. Further preferred compounds correspond to the formula:

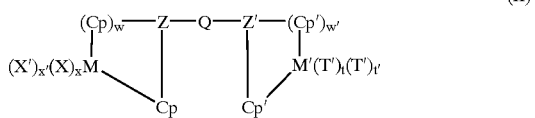

(II)

wherein

Z, Z', M, M', X, X', T, T', w, w', x, x', t, and t' are as previously defined;

Cp and Cp', independently are cyclic $C_5R'_4$ groups bound to Z or Z' respectively and bound to M or M' respectively by means of delocalized π-electrons, wherein R', independently each occurrence, is hydrogen, hydrocarbyl, silyl, halo, fluorohydrocarbyl, hydrocarbyloxy, hydrocarbylsiloxy, N,N-di (hydrocarbylsilyl)amino, N-hydrocarbyl-N-silylamino, N,N-di(hydrocarbyl)amino, hydrocarbyleneamino, di(hydrocarbyl)phosphino, hydrocarbylsulfido; or hydrocarbyloxy-substituted hydrocarbyl, said R' having up to 20 nonhydrogen atoms, and optionally, two such R' substituents may be joined together thereby causing Cp or Cp' to have a fused ring structure; and Q is a linear or cyclic hydrocarbylene, or silane group or a nitrogen, oxygen, or halo substituted derivative thereof, said Q having up to 20 nonhydrogen atoms.

More preferred metal coordination complexes according to the present invention correspond to the formula:

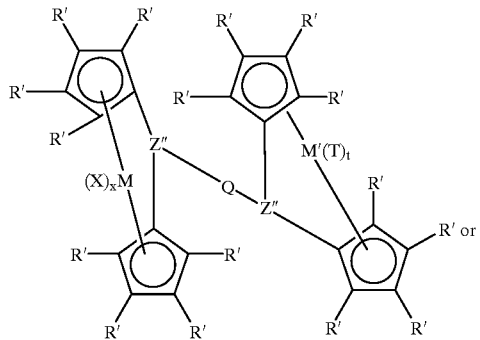

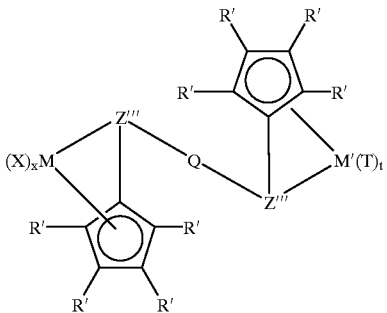

-continued wherein:

R' each occurrence is hydrogen, hydrocarbyl, silyl, germyl, halo, cyano, halohydrocarbyl, hydrocarbyloxy, hydrocarbylsiloxy, di(hydrocarbylsilyl)amino, hydrocarbylsilylamino, di(hydrocarbyl)amino, hydrocarbyleneamino, di(hydrocarbyl)phosphino, hydrocarbylsulfido; or hydrocarbyloxy-substituted hydrocarbyl, said R' having up to 20 nonhydrogen atoms, and optionally, two R' groups together form a divalent derivative thereof connected to adjacent positions of the cyclopentadienyl ring thereby forming a fused ring structure, or R' in one occurrence per cyclopentadienyl system is a covalent bond to Q;

Z" independently each occurrence is a trivalent group selected from $SiR^*$, $CR^*$, $SiR^*SiR^*_2$, $CR^*CR^*_2$, $CR^*SiR^*_2$, $CR^*_2SiR^*$, or $GeR^*$; wherein $R^*$ each occurrence is independently hydrogen, hydrocarbyl, silyl, halogenated alkyl, or halogenated aryl, said $R^*$ having up to 12 non-hydrogen atoms;

Z''' independently each occurrence is —Z"Y'—, wherein:

Y' is —O—, —S—, —NR"—, —PR"—, —OR", or —NR"$_2$ (and with respect to —OR" and —NR"$_2$, one bond is a dative bond through the available electron pair), wherein R" is hydrogen, hydrocarbyl, silyl, or silylhydrocarbyl of up to 20 atoms not counting hydrogen;

M and M' independently are Ti, Zr or Hf;

X and T, independently are halide, hydrocarbyl or two X groups together or two T groups together are a conjugated diene group, said X and T groups having up to 20 atoms not counting hydrogen; and Q is a linear or cyclic hydrocarbylene group, silane group, or silyl substituted hydrocarbylene group, or a nitrogen, oxygen, or halo substituted derivative thereof, said Q having up to 20 atoms not counting hydrogen.

Preferably, R' independently each occurrence is hydrogen, hydrocarbyl, silyl, fluorophenyl, hydrocarbyloxy, N,N-di (hydrocarbyl)amino, hydrocarbyleneamino, or hydrocarbyloxy-substituted hydrocarbyl, said R' having up to 20 non-hydrogen atoms, or two adjacent R' groups are joined together forming part of a fused ring system. Most preferably, R' is hydrogen, methyl, ethyl, propyl, butyl, pentyl, hexyl, (including where appropriate all isomers), cyclopentyl, cyclohexyl, norbornyl, benzyl, phenyl, N,N-di (methyl)amino, pyrrolyl, pyrrolidinyl, or two R' groups are linked together, the entire $C_5R'_4$ group thereby forming an indenyl, tetrahydroindenyl, fluorenyl, tetrahydrofluorenyl, indacenyl, or octahydrofluorenyl group, or a $C_{1-6}$ hydrocarbyl-substituted, N,N-di(methyl)amino-substituted, pyrrolyl, or pyrrolidinyl-substituted derivative thereof.

Examples of suitable X or T groups for all of the foregoing structural depictions of the invention include single atomic groups including hydride or halide, as well as multi-atomic groups such as hydrocarbyl, hydrocarbyloxy, dihydrocarbylamido (including cyclic hydrocarbyleneamido groups) and halo, amino, or phosphino substituted derivatives thereof, said multi-atomic groups containing up to 20 nonhydrogen atoms. Specific examples include chloride, methyl, benzyl, allyl, N,N-dimethylamido, pyrrolinado, pyrrolidinado, (N,N-dimethylamino)benzyl, phenyl, methoxide, ethoxide, isopropoxide and isobutoxide. Most preferably X and T are chloride, methyl, N,N-dimethylamido, or benzyl.

In the embodiments wherein two X or wherein two T groups together form a diene group or substituted diene group, such group may form a α-complex with M or M' or the diene may form a σ-complex with M or M'. In such complexes M and M' are preferably Group 4 metals, most preferably Ti. In such complexes in which the diene is associated with the metal as a α-complex, the metal is in the +4 formal oxidation state and the diene and metal together form a metallocyclopentene. In such complexes in which the diene is associated with the metal as a π-complex, the metal is in the +2 formal oxidation state, and the diene normally assumes a s-trans configuration or an s-cis configuration in which the bond lengths between the metal and the four carbon atoms of the conjugated diene are nearly equal. The dienes of complexes wherein the metal is in the +2 formal oxidation state are coordinated via π-complexation through the diene double bonds and not through a metallocycle resonance form containing σ-bonds. The nature of the bond is readily determined by X-ray crystallography or by NMR spectral characterization according to the techniques of Yasuda, et al., *Organometallics*, 1, 388 (1982), (Yasuda I); Yasuda, et al. *Acc. Chem. Res.*, 18, 120 (1985), (Yasuda II); Erker, et al. , *Adv. Organomet. Chem.*, 24, 1 (1985)(Erker, et al. (I)); and U.S. Pat. No. 5,198,401. By the term "π-complex" is meant both the donation and back acceptance of electron density by the ligand are accomplished using ligand π-orbitals. Such dienes are referred to as being π-bound. It is to be understood that the present complexes may be formed and utilized as mixtures of the π-complexed and σ-complexed diene compounds.

The formation of the diene complex in either the π or σ state depends on the choice of the diene, the specific metal complex and the reaction conditions employed in the preparation of the complex. Generally, terminally substituted dienes favor formation of π-complexes and internally substituted dienes favor formation of σ-complexes. Especially useful dienes for such complexes are compounds that do not decompose under reaction conditions used to prepare the complexes of the invention. Under subsequent polymerization conditions, or in the formation of catalytic derivatives of the present complexes, the diene group may undergo chemical reactions or be replaced by another ligand.

Examples of suitable dienes (two X or T groups taken together) include: butadiene, 1,3-pentadiene, 1,3-hexadiene, 2,4-hexadiene, 1,4-diphenyl-1,3-butadiene, 3-methyl-1,3-pentadiene, 1,4-dibenzyl-1,3-butadiene, 1,4-ditolyl-1,3-butadiene, and 1,4-bis(trimethylsilyl)-1,3-butadiene.

Examples of the preferred metal complexes according to the present invention include compounds wherein R' is methyl, ethyl, propyl, butyl, pentyl, hexyl, (including all isomers of the foregoing where applicable), cyclododecyl, norbornyl, benzyl, phenyl, Q is 1,2-ethanediyl, 1,4-butanediyl, 1,6-hexanediyl or silane, Z" is hydrocarbylsilane, most preferably methylsilanetriyl; and the cyclic delocalized π-bonded group is cyclopentadienyl, tetramethylcyclopentadienyl, indenyl, tetrahydroindenyl, 2-methylindenyl, 2,3-dimethylindenyl, 2-methyl-4-phenylindenyl, 3-N,N-dimethylaminoindenyl, 3-(pyrrolyl) inden-1-yl, 3-(pyrrolidinyl)inden-1-yl, fluorenyl, tetrahydrofluorenyl, indacenyl or octahydrofluorenyl group; M and M' are titanium or zirconium in the +2 or +4 formal oxidation state.

Examples of the foregoing more further preferred dinuclear complexes are of the formula:

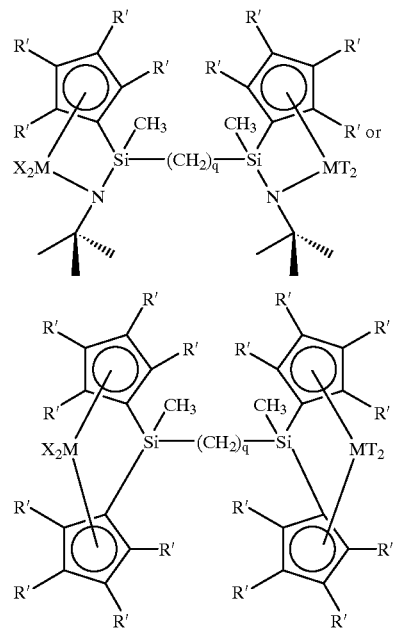

wherein

M is titanium or zirconium;

q is an integer from 2 to 10;

R' is methyl or all R' groups collectively with the cyclopentadienyl group form a 2,3,4,6-tetramethylinden-1-yl, 3-(N-pyrrolidinyl)inden-1-yl, or a 2-methyl-4-phenylinden-1-yl group; and X and T, independently each occurrence, are chloride, methyl, benzyl or 2 X groups or two T groups together form a 1,4-diphenyl-1,3-butadiene or 1,3-pentadiene group.

Specific examples of the foregoing metal complexes include:

Titanium Complexes:

1,2-bis[(1-N-(t-butyl)amido)-1-methyl-1-(tetramethylcyclopentadien-diyl)silantitanium dichloride] ethane, 1,6-bis[(1-N-(t-butyl)amido)-1-methyl-1-(tetramethylcyclopentadien-diyl)silantitanium dichloride] hexane, 1,2-bis[(1-N-(t-butyl)amido)-1-methyl-1-(3-(1-pyrrolidinyl)-1H-inden-1-diyl)silantitanium dichloride] ethane, 1,6-bis[(1-N-(t-butyl)amido)-1-methyl-1-(3-(1-pyrrolidinyl)-1H-inden-1-diyl)silantitanium dichloride] hexane, 1,2-bis[(1-N-(t-butyl)amido)-1-methyl-1-(2,3,4,6-tetramethylinden-1-diyl)silantitanium dichloride]ethane, 1,6-bis[(1-N-(t-butyl)amido)-1-methyl-1-(2,3,4,6-tetramethylinden-1-diyl)silantitanium dichloride]hexane, 1,2-bis[(1-N-(t-butyl)amido)-1-methyl-1-(2-methyl-4-phenylinden-1-diyl)silantitanium dichloride]ethane, 1,6-bis[(1-N-(t-butyl)amido)-1-methyl-1-(2-methyl-4-phenylinden-1-diyl)silantitanium dichloride]hexane,
1,2-bis[(1-N-(t-butyl)amido)-1-methyl-1-(tetramethylcyclopentadien-diyl)silantitanium dimethyl]ethane,
1,6-bis[(1-N-(t-butyl)amido)-1-methyl-1-(tetramethylcyclopentadien-diyl)silantitanium dimethyl]hexane,
1,2-bis[(1-N-(t-butyl)amido)-1-methyl-1-(3-(1-pyrrolidinyl)-1H-inden-1-diyl)silantitanium dimethyl]ethane,
1,6-bis[(1-N-(t-butyl)amido)-1-methyl-1-(3-(1-pyrrolidinyl)-1H-inden-1-diyl)silantitanium dimethyl]hexane,
1,2-bis[(1-N-(t-butyl)amido)-1-methyl-1-(2,3,4,6-tetramethylinden-1-diyl)silantitanium dimethyl]ethane,
1,6-bis[(1-N-(t-butyl)amido)-1-methyl-1-(2,3,4,6-tetramethylinden-1-diyl)silantitanium dimethyl]hexane,
1,2-bis[(1-N-(t-butyl)amido)-1-methyl-1-(2-methyl-4-phenylinden-1-diyl)silantitanium dimethyl]ethane,
1,6-bis[(1-N-(t-butyl)amido)-1-methyl-1-(2-methyl-4-phenylinden-1-diyl)silantitanium dimethyl]hexane,
1,2-bis[(1-N-(t-butyl)amido)-1-methyl-1-(tetramethylcyclopentadien-diyl)silantitanium dibenzyl]ethane,
1,6-bis[(1-N-(t-butyl)amido)-1-methyl-1-(tetramethylcyclopentadien-diyl)silantitanium dibenzyl]hexane,
1,2-bis[(1-N-(t-butyl)amido)-1-methyl-1-(3-(1-pyrrolidinyl)-1H-inden-1-diyl)silantitanium dibenzyl]ethane,
1,6-bis[(1-N-(t-butyl)amido)-1-methyl-1-(3-(1-pyrrolidinyl)-1H-inden-1-diyl)silantitanium dibenzyl]hexane,
1,2-bis[(1-N-(t-butyl)amido)-1-methyl-1-(2,3,4,6-tetramethylinden-1-diyl)silantitanium dibenzyl]ethane,
1,6-bis[(1-N-(t-butyl)amido)-1-methyl-1-(2,3,4,6-tetramethylinden-1-diyl)silantitanium dibenzyl]hexane,
1,2-bis[(1-N-(t-butyl)amido)-1-methyl-1-(2-methyl-4-phenylinden-1-diyl)silantitanium dibenzyl]ethane,
1,6-bis[(1-N-(t-butyl)amido)-1-methyl-1-(2-methyl-4-phenylinden-1-diyl)silantitanium dibenzyl]hexane,
1,2-bis[(1-N-(t-butyl)amido)-1-methyl-1-(tetramethylcyclopentadien-diyl)silantitanium (II) 1,4-diphenyl-1-3-butadiene]ethane,
1,6-bis[(1-N-(t-butyl)amido)-1-methyl-1-(tetramethylcyclopentadien-diyl)silantitanium (II) 1,4-diphenyl-1-3-butadiene]hexane,
1,2-bis[(1-N-(t-butyl)amido)-1-methyl-1-(3-(1-pyrrolidinyl)-1H-inden-1-diyl)silantitanium (II) 1,4-diphenyl-1-3-butadiene]ethane,
1,6-bis[(1-N-(t-butyl)amido)-1-methyl-1-(3-(1-pyrrolidinyl)-1H-inden-1-diyl)silantitanium (II) 1,4-diphenyl-1-3-butadiene]hexane,
1,2-bis[(1-N-(t-butyl)amido)-1-methyl-1-(2,3,4,6-tetramethylinden-1-diyl)silantitanium (II) 1,4-diphenyl-1-3-butadiene]ethane,
1,6-bis[(1-N-(t-butyl)amido)-1-methyl-1-(2,3,4,6-tetramethylinden-1-diyl)silantitanium (II) 1,4-diphenyl-1-3-butadiene]hexane,
1,2-bis[(1-N-(t-butyl)amido)-1-methyl-1-(2-methyl-4-phenylinden-1-diyl)silantitanium (II) 1,4-diphenyl-1-3-butadiene]ethane,
1,6-bis[(1-N-(t-butyl)amido)-1-methyl-1-(2-methyl-4-phenylinden-1-diyl)silantitanium (II) 1,4-diphenyl-1-3-butadiene]hexane,
1,2-bis[(1-N-(t-butyl)amido)-1-methyl-1-(tetramethylcyclopentadien-diyl)silantitanium (II) 1,3-pentadiene]ethane,
1,6-bis[(1-N-(t-butyl)amido)-1-methyl-1-(tetramethylcyclopentadien-diyl)silantitanium (II) 1,3-pentadiene]hexane,
1,2-bis[(1-N-(t-butyl)amido)-1-methyl-1-(3-(1-pyrrolidinyl)-1H-inden-1-diyl)silantitanium (II) 1,3-pentadiene]ethane,
1,6-bis[(1-N-(t-butyl)amido)-1-methyl-1-(3-(1-pyrrolidinyl)-1H-inden-1-diyl)silantitanium (II) 1,3-pentadiene]hexane,
1,2-bis[(1-N-(t-butyl)amido)-1-methyl-1-(2,3,4,6-tetramethylinden-1-diyl)silantitanium (II) 1,3-pentadiene]ethane,
1,6-bis[(1-N-(t-butyl)amido)-1-methyl-1-(2,3,4,6-tetramethylinden-1-diyl)silantitanium (II) 1,3-pentadiene]hexane,
1,2-bis[(1-N-(t-butyl)amido)-1-methyl-1-(2-methyl-4-phenylinden-1-diyl)silantitanium (II) 1,3-pentadiene]ethane, and
1,6-bis[(1-N-(t-butyl)amido)-1-methyl-1-(2-methyl-4-phenylinden-1-diyl)silantitanium (II) 1,3-pentadiene]hexane.

Zirconium Complexes:
1,2-bis[1,1-bis(tetramethylcyclopentadiendiyl)-1-methylsilanzirconium dichloride]ethane,
1,6-bis[1,1-bis(tetramethylcyclopentadiendiyl)-1-methylsilanzirconium dichloride]hexane,
1,2-bis[1,1-bis(3-(1-pyrrolidinyl)-1-H-inden-1-diyl)-1-methylsilanzirconium dichloride]ethane,
1,6-bis[1,1-bis(3-(1-pyrrolidinyl)-1-H-inden-1-diyl)-1-methylsilanzirconium dichloride]hexane,
1,2-bis[1,1-bis(2,3,4,6-tetramethyl)-1-H-inden-1-diyl)-1-methylsilanzirconium dichloride]ethane,
1,6-bis[1,1-bis(2,3,4,6-tetramethyl)-1-H-inden-1-diyl)-1-methylsilanzirconium dichloride]hexane,
1,2-bis[1,1-bis(2-methyl-4-phenyl)-1-H-inden-1-diyl)-1-methylsilanzirconium dichloride]ethane,
1,6-bis[1,1-bis(2-methyl-4-phenyl)-1-H-inden-1-diyl)-1-methylsilanzirconium dichloride]hexane,
1,2-bis[1,1-bis(tetramethylcyclopentadiendiyl)-1-methylsilanzirconium dimethyl]ethane,
1,6-bis[1,1-bis(tetramethylcyclopentadiendiyl)-1-methylsilanzirconium dimethyl]hexane,
1,2-bis[1,1-bis(3-(1-pyrrolidinyl)-1-H-inden-1-diyl)-1-methylsilanzirconium dimethyl]ethane,
1,6-bis[1,1-bis(3-(1-pyrrolidinyl)-1-H-inden-1-diyl)-1-methylsilanzirconium dimethyl]hexane,
1,2-bis[1,1-bis(2,3,4,6-tetramethyl)-1-H-inden-1-diyl)-1-methylsilanzirconium dimethyl]ethane,
1,6-bis[1,1-bis(2,3,4,6-tetramethyl)-1-H-inden-1-diyl)-1-methylsilanzirconium dimethyl]hexane,
1,2-bis[1,1-bis(2-methyl-4-phenyl)-1-H-inden-1-diyl)-1-methylsilanzirconium dimethyl]ethane,
1,6-bis[1,1-bis(2-methyl-4-phenyl)-1-H-inden-1-diyl)-1-methylsilanzirconium dimethyl]hexane,
1,2-bis[1,1-bis(tetramethylcyclopentadiendiyl)-1-methylsilanzirconium dibenzyl]ethane,
1,6-bis[1,1-bis(tetramethylcyclopentadiendiyl)-1-methylsilanzirconium dibenzyl]hexane,
1,2-bis[1,1-bis(3-(1-pyrrolidinyl)-1-H-inden-1-diyl)-1-methylsilanzirconium dibenzyl]ethane,
1,6-bis[1,1-bis(3-(1-pyrrolidinyl)-1-H-inden-1-diyl)-1-methylsilanzirconium dibenzyl]hexane,
1,2-bis[1,1-bis(2,3,4,6-tetramethyl)-1-H-inden-1-diyl)-1-methylsilanzirconium dibenzyl]ethane,
1,6-bis[1,1-bis(2,3,4,6-tetramethyl)-1-H-inden-1-diyl)-1-methylsilanzirconium dibenzyl]hexane,
1,2-bis[1,1-bis(2-methyl-4-phenyl)-1-H-inden-1-diyl)-1-methylsilanzirconium dibenzyl]ethane, 1,6-bis[1,1-bis(2-methyl-4-phenyl)-1-H-inden-1-diyl)-1-methylsilanzirconium dibenzyl]hexane, 1,2-bis[1,1-bis(tetramethylcyclopentadiendiyl)-1-methylsilanzirconium (II) 1,4-diphenyl-1-3-butadiene] ethane, 1,6-bis[1,1-bis(tetramethylcyclopentadiendiyl)-1-methylsilanzirconium (II) 1,4-diphenyl-1-3-butadiene] hexane, 1,2-bis[1,1-bis(3-(1-pyrrolidinyl)-1-H-inden-1-diyl)-1-methylsilanzirconium (II) 1,4-diphenyl-1-3-butadiene] ethane, 1,6-bis[1,1-bis(3-(1-pyrrolidinyl)-1-H-inden-1-diyl)-1-methylsilanzirconium (II) 1,4-diphenyl-1-3-butadiene] hexane, 1,2-bis[1,1-bis(2,3,4,6-tetramethyl)-1-H-inden-1-diyl)-1-methylsilanzirconium (II) 1,4-diphenyl-1-3-butadiene] ethane, 1,6-bis[1,1-bis(2,3,4,6-tetramethyl)-1-H-inden-1-diyl)-1-methylsilanzirconium (II) 1,4-diphenyl-1-3-butadiene] hexane, 1,2-bis[1,1-bis(2-methyl-4-phenyl)-1-H-inden-1-diyl)-1-methylsilanzirconium (II) 1,4-diphenyl-1-3-butadiene] ethane, and 1,6-bis[1,1-bis(2-methyl-4-phenyl)-1-H-inden-1-diyl)-1-methylsilanzirconium (II) 1,4-diphenyl-1-3-butadiene] hexane.

In general, the complexes of the present invention can be prepared by combining the dimetallated or diGrignard compound derived from the group Q in the resulting complex, with the precursor complex or mixture of complexes in a suitable noninterfering solvent at a temperature from −100° C. to 300° C., preferably from −78 to 130° C., most preferably from −10 to 120° C. More particularly, the complexes can be prepared by lithiating a compound of the formula: HCp—Z—Q—Z—CpH, such as 1,2-ethane (bisinden-1-yl)methylchlorosilane), reacting the resulting dimetallated compound with 2 equivalents of an amine, preferably t-butylamine, and reacting the resulting product with a metal halide such as titanium or zirconium tetrachloride or titanium or zirconium trichloride, and optionally oxidizing the resulting metal complex. Similarly, the bis (bridged metal complexes) are prepared by lithiating a compound of the formula: (HCp)(HW)Z—Q—Z(WH) (CpH), such as 1,2-ethanebis[bis(inden-1-yl)methylsilane] and reacting the resulting product directly with the metal halide salt. The corresponding hydrocarbyl or diene derivative may be prepared by known exchange with the metal hydrocarbyl or conjugated diene under reducing conditions. Alternatively, the desired bimetal dihydrocarbyl complex can be directly formed by reaction with a titanium or zirconium tetraamide, especially titanium tetra(N,N-dimethylamide) or zirconium tetra(N,N-dimethylamide), under ring formation conditions, followed by reaction with excess aluminum trialkyl to form the desired dialkyl derivative. Modifications of the foregoing preparation procedure to prepare alternative compound of the invention may be employed by the skilled artisan without departing from the scope of the present invention.

Suitable reaction media for the formation of the complexes are aliphatic and aromatic hydrocarbons and halohydrocarbons, ethers, and cyclic ethers. Examples include straight and branched-chain hydrocarbons such as $C_{4-12}$ alkanes and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, xylene, and $C_{1-4}$ dialkyl ethers, $C_{1-4}$ dialkyl ether derivatives of (poly) alkylene glycols, and tetrahydrofuran. Mixtures of the foregoing list of suitable solvents are also suitable.

The recovery procedure involves separation of the resulting alkali metal or alkaline earth metal salt and devolatilization of the reaction medium. Extraction into a secondary solvent may be employed if desired. Alternatively, if the desired product is an insoluble precipitate, filtration or other separation technique may be employed.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or diisobutylalumoxane; strong Lewis acids (the term "strong" as used herein defines Lewis acids which are not Bronsted acids), such as $C_{1-30}$ hydrocarbyl substituted Group 13 compounds, especially tri (hydrocarbyl)aluminum- or tri(hydrocarbyl)boron compounds, and halogenated derivatives thereof, having from 1 to 10 carbons in each hydrocarbyl or halogenated hydrocarbyl group, more especially perfluorinated tri(aryl)boron compounds, and most especially tris(pentafluorophenyl) borane or 1,4-tetrafluorophenylene {bis(bis (pentafluorophenyl)borane}; nonpolymeric, ionic, compatible, noncoordinating, activating compounds (including the use of such compounds under oxidizing conditions); and combinations thereof. The foregoing activating cocatalysts and activating techniques have been previously taught with respect to different metal complexes in the following references: EP-A-277,003, U.S. Pat. Nos. 5,153,157, 5,064,802, 5,321,106, 5,721,185, 5,425,872, 5,350,723, WO97-35893 (equivalent to U.S. Ser. No. 08/818,530, filed Mar. 14, 1997), and U.S. provisional application No. 60/054586, filed Sep. 15, 1997.

Combinations of strong Lewis acids, especially the combination of a trialkyl aluminum compound having from 1 to 4 carbons in each alkyl group and a halogenated tri (hydrocarbyl)boron compound having from 1 to 10 carbons in each hydrocarbyl group, especially tris (pentafluorophenyl)borane; further combinations of such strong Lewis acid mixtures with a polymeric or oligomeric alumoxane; and combinations of a single strong Lewis acid, especially tris(pentafluorophenyl)borane with a polymeric or oligomeric alumoxane are especially desirable activating cocatalysts.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis, are used such that electrolysis byproducts that would render the metal complex catalytically inactive are not substantially formed during the reaction. More particularly, suitable solvents are materials that are liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (ortho, meta, or para isomers), dimethoxyethane, and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and an inert, compatible, noncoordinating anion, $A^-$. Preferred supporting electrolytes are salts corresponding to the formula $$G^+A^-$$

wherein:

G$^+$ is a cation which is nonreactive towards the starting and resulting complex; and $A^-$ is a noncoordinating, compatible anion.

Examples of cations, G$^+$, include tetrahydrocarbyl substituted ammonium or phosphonium cations having up to 40 nonhydrogen atoms. A preferred cation is the tetra-n-butylammonium cation.

During activation of the complexes of the present invention by bulk electrolysis the cation of the supporting electrolyte passes to the counter electrode and $A^-$ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoro-aryl)borates having from 1 to 10 carbons in each hydrocarbyl group, especially tetra-n-butylammonium tetrakis(pentafluorophenyl)borate.

Suitable activating compounds useful as a cocatalyst in one embodiment of the present invention comprise a cation which is a Bronsted acid capable of donating a proton, and an inert, compatible, noncoordinating, anion, $A^-$. Preferred anions are those containing a single coordination complex comprising a charge-bearing metal or metalloid core which anion is capable of balancing the charge of the active catalyst species (the metal cation) which is formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially. Therefore, said single boron atom compounds are preferred.

Preferably such cocatalysts may be represented by the following general formula:

$$(L^*-H)_d^+(A^{d-})$$

wherein:

L* is a neutral Lewis base;

(L*–H)$^+$ is a Bronsted acid;

$A^{d-}$ is a noncoordinating, compatible anion having a charge of d–, and d is an integer from 1 to 3.

More preferably $A^{d-}$ corresponds to the formula:

$$[M'^{k+}Q'_{n'}]^{d-}$$

wherein:

k is an integer from 1 to 3;

n' is an integer from 2 to 6;

n'–k=d;

M' is an element selected from Group 13 of the Periodic Table of the Elements; and Q' independently each occurrence is an hydride, dialkylamido, halide, alkoxide, aryloxide, hydrocarbyl, or halosubstituted-hydrocarbyl radical, said Q' having up to 20 carbons with the proviso that in not more than one occurrence is Q' halide.

In a more preferred embodiment, d is one, that is the counter ion has a single negative charge and corresponds to the formula $A^-$. Activating cocatalysts comprising boron which are particularly useful in the preparation of catalysts of this invention may be represented by the following general formula:

$$[L^*-H]^+[BQ''_4]^-$$

wherein:

L* is as previously defined;

B is boron in a valence state of 3; and

Q" is a fluorinated $C_{1-20}$ hydrocarbyl group.

Most preferably, Q" is in each occurrence a fluorinated aryl group, especially a pentafluorophenyl group.

Illustrative, but not limiting examples of boron compounds which may be used as an activating cocatalyst in the preparation of the improved catalysts of this invention are tri-substituted ammonium salts such as:
trimethylammonium tetrakis(pentafluorophenylborate,
dimethylanilinium tetrakis(pentafluorophenylborate,
dimethyltetradecylammonium tetrakis(pentafluorophenylborate,
dimethyhexadecylammonium tetrakis(pentafluorophenylborate,
dimethyloctadecylammonium tetrakis(pentafluorophenylborate,
methylbis(tetradecyl)ammonium tetrakis(pentafluorophenylborate,
methylbis(hexadecyl)ammonium tetrakis(pentafluorophenylborate,
methylbis(octadecyl)ammonium tetrakis(pentafluorophenylborate, and mixtures thereof.

Another suitable ion forming, activating cocatalyst comprises a salt of a cationic oxidizing agent and a noncoordinating, compatible anion represented by the formula:

$$(Ox^{e+})_d(A^{d-})_e$$

wherein:

$Ox^{e+}$ is a cationic oxidizing agent having a charge of e+;

e is an integer from 1 to 3; and $A^{d-}$, and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula:

$^+A^-$ wherein:

$^-$ is a $C_{1-20}$ carbenium ion; and $A^-$ is as previously defined. A preferred carbenium ion is the trityl cation, that is triphenylcarbenium.

The foregoing activating technique and ion forming cocatalysts are also preferably used in combination with a tri(hydrocarbyl)aluminum compound having from 1 to 4 carbons in each hydrocarbyl group, an oligomeric or polymeric alumoxane compound, or a mixture of a tri(hydrocarbyl)aluminum compound having from 1 to 4 carbons in each hydrocarbyl group and a polymeric or oligomeric alumoxane.

The molar ratio of catalyst/cocatalyst employed preferably ranges from 1:10,000 to 100:1, more preferably from 1:5000 to 10:1, most preferably from 1:1000 to 1:1. In a particularly preferred embodiment of the invention the cocatalyst can be used in combination with a $C_{3-30}$ trihydrocarbyl aluminum compound, $C_{3-30}$ (hydrocarbyoloxy) dihydrocarbylaluminum compound, or oligomeric or polymeric alumoxane. Which aluminum compounds are employed for their beneficial ability to scavenge impurities such as oxygen, water, and aldehydes from the polymerization mixture. Preferred aluminum compounds include $C_{2-6}$ trialkyl aluminum compounds, especially those wherein the alkyl groups are ethyl, propyl, isopropyl, n-butyl, isobutyl, pentyl, neopentyl, or isopentyl, and methylalumoxane, modified methylalumoxane and diisobutylalumoxane. The molar ratio of aluminum compound to metal complex is preferably from 1:10,000 to 1000:1, more preferably from 1:5000 to 100:1, most preferably from 1:100 to 100:1.

The catalysts may exist as cationic derivatives of the dinuclear complexes, as zwitterionic derivatives thereof, or in an as yet undetermined relationship with the cocatalyst activator.

The catalysts may be used to polymerize ethylenically and/or acetylenically unsaturated monomers having from 2 to 20 carbon atoms either alone or in combination. Preferred monomers include the $C_{2-10}$ α-olefins especially ethylene, propylene, isobutylene, 1-butene, 1-hexene, 4-methyl-1-pentene, and 1-octene and mixtures thereof. Other preferred monomers include vinylcyclohexene, vinylcyclohexane, styrene, $C_{1-4}$ alkyl substituted styrene, tetrafluoroethylene, vinylbenzocyclobutane, ethylidenenorbornene and 1,4-hexadiene.

In general, the polymerization may be accomplished at conditions well known in the prior art for Ziegler-Natta or Kaminsky-Sinn type polymerization reactions, that is, temperatures from 0–250° C. and pressures from atmospheric to 3000 atmospheres. Suspension, solution, slurry, gas phase or high pressure, whether employed in batch or continuous form or under other process conditions, may be employed if desired. For example, the use of condensation in a gas phase polymerization is a especially desirable mode of operation for use of the present catalysts. Examples of such well known polymerization processes are depicted in WO 88/02009, U.S. Pat. Nos. 5,084,534, 5,405,922, 4,588,790, 5,032,652, 4,543,399, 4,564,647, 4,522,987, and elsewhere, which teachings disclose conditions that can be employed with the polymerization catalysts of the present invention. A support, especially silica, alumina, or a polymer (especially polytetrafluoroethylene or a polyolefin) may be employed, and desirably is employed when the catalysts are used in a gas phase polymerization process with or without condensation. Methods for the preparation of supported catalysts are disclosed in numerous references, examples of which are U.S. Pat. Nos. 4,808,561, 4,912,075, 5,008,228, 4,914,253, and 5,086,025 and are suitable for the preparation of supported catalysts of the present invention.

In most polymerization reactions the molar ratio of catalyst:polymerizable compounds employed is from $10^{-12}$:1 to $10^{-1}$:1, more preferably from $10^{-12}$:1 to $10^{-5}$:1.

Suitable solvents for solution, suspension, slurry or high pressure polymerization processes are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and aromatic and alkyl-substituted aromatic compounds such as benzene, toluene, and xylene. Suitable solvents also include liquid olefins which may act as monomers or comonomers including ethylene, propylene, butadiene, cyclopentene, 1-hexene, 3-methyl-1-pentene, 4-methyl-1-pentene, 1,4-hexadiene, 1-octene, 1-decene, styrene, divinylbenzene, allylbenzene, and vinyltoluene (including all isomers alone or in admixture). Mixtures of the foregoing are also suitable.

Having described the invention the following examples are provided as further illustration thereof and are not to be construed as limiting. Unless stated to the contrary all parts and percentages are expressed on a weight basis. The invention herein disclosed may be performed in the absence of any reagent not specifically described. The term "overnight", if used, refers to a time of approximately 16–18 hours, "room temperature", if used, refers to a temperature of about 20–25° C., and "mixed alkanes" or "alkanes" refers to a mixture of mostly $C_6$–$C_{12}$ isoalkanes available commercially under the trademark Isopar E™ from Exxon Chemicals Inc.

All manipulation of air sensitive materials was performed in an argon filled, vacuum atmospheres, glove box or on a high vacuum line using standard Shlenk techniques. Solvents were purified by passage through columns packed with activated alumina (Kaiser A-2) and supported copper (Engelhard, Cu-0224 S). Anhydrous $C_6D_6$ and $CH_2Cl_2$ were purchased from Aldrich and used as received. NMR spectra were recorded on a Varian XL-300 instrument ($^1H$, 300 MHz; $^{13}C\{^1H\}$, 75 MHz). $^1H$ and $^{13}C\{^1H\}$ NMR spectra are reported relative to tetramethylsilane and are referenced to the residual solvent peak.

MeLi, bis(dichloromethylsilyl)ethane, triethylamine and tert-butylamine were purchased from Aldrich and used as received. Bis(dichloromethylsilyl)hexane (United Chemical Technologies), n-butyllithium (ACROS) and 2-methyl-4-phenylindene (Boulder Scientific) were used as received. 1-N-pyrrolidineindene was prepared via the route of Noland, et al., *JOC,* 1981, 46, (1940) It's lithium salt, (1-(1-pyrrolidinyl)-1H-indenyl)lithium, was prepared by reaction with butyllithium in hexanes and recovered by filtration.

EXAMPLE 1

($\mu$-((1,1'-(1,6-hexanediyl)bis(N-(1,1-dimethylethyl)-1-methyl-1-((1,2,3,3a,7a-$\eta$)-3-(1-pyrrolidinyl)-1H-inden-1-yl)silanaminato-$\kappa$N)(4-)))) tetrachlorodititanium

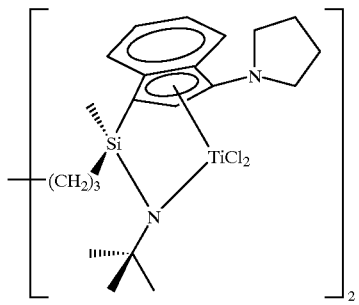

A) 1,1'-(1,6-hexanediyl)bis(1-chloro-N-(1,1-dimethylethyl)-1-methyl)-silanamine

To a –10° C. solution of 1,6-bis(chloromethylsilyl)hexane (25.00 g, 80.1 mmol) and triethylamine (24.6 mL, 0.176 mole) in 250 mL of dichloromethane was added dropwise over 1 hour a solution of tert-butylamine (16.8 mL, 0.160 mole) in 100 mL of dichloromethane. The suspension was allowed to warm to room temperature. After stirring overnight, most to the volatiles were removed in vacuo. The product was extracted into 175 mL of hexanes, filtered and the hexanes removed in vacuo to leave 29.5 g (96 percent yield) of 1,1'-(1,6-hexanediyl)bis(1-chloro-N-(1,1-dimethylethyl)-1-methyl)silanamine as a pale-pink viscous liquid.

$^1H$ NMR ($C_6D_6$): 1.35 (m, 4H), 1.24 (m, 4H), 1.13 (s, 18H), 1.03 (br s, 2H), 0.75 (m, 4H), 0.33 (s, 6H). $^{13}C\{^1H\}$ ($C_6D_6$): 50.35, 33.42, 32.95, 23.74, 20.34, 3.12.

B) 1,1'-(1,6-hexanediyl)bis(N-(1,1-dimethylethyl)-1-methyl-1-(3-(1-pyrrolidinyl)-1H-inden-1-yl)-silanamine To a –30° C. solution of 1,6-bis(N-(tert-butyl)-1-chloro-1-methylsilanamine)hexane (1.50 g, 3.89 mmol) in 20 mL of THF was added a precooled (–30° C.) solution of (1-(1-pyrrolidinyl)-1H-indenyl)lithium (1.49 g, 7.78 mmol) in 10 mL of THF. The reaction was allowed to warm to room temperature as it gradually darkened and changed to a deep-red/purple solution with slight green flourescence. After 16 hours, the volatiles were removed in vacuo and 50 mL of hexanes added. The suspension was filtered and hexanes removed from the filtrate in vacuo to leave 2.5 g (92 percent yield) of 1,1'-(1,6-hexanediyl)bis(N-(1,1-dimethylethyl)-1-methyl-1-(3-(1-pyrrolidinyl)-1H-inden-1-yl)-silanamine as a red/purple oil.

$^1H$ NMR ($C_6D_6$): 7.71 (m, 4H), 7.27 (m, 4H), 5.47/5.43 (2 s, 2H, isomers), 3.51 (s, 2H), 3.29 (br s, 8H), 1.64 (sh m, 8H), 1.30 (m, 8H), 1.11 (set of several sharp peaks, 18H), 0.616 (br s, 2H), 0.50 (s, 4H), 0.20/0.04 (2 singlets, 6H, isomers). $^{13}C\{^1H\}$ ($C_6D_6$): 149.21, 146.99, 141.66, 124.85, 124.63, 123.95, 123.82, 120.95, 105.11, 50.86, 49.54, 43.20 (m), 34.05, 25.42, 24.51, 17.25/16.19 (isomers), –0.71/–1.88 (isomers).

C) 1,1'-(1,6-hexanediyl)bis(N-(1,1-dimethylethyl)-1-methyl-i-(3-(1-pyrrolidinyl)-1H-inden-1-yl)t$^2$, (deloc-1,2,3,3a,7a:1', 2',3',3',3'a,7'a)-silanamine, dilithium, dilithium salt To a solution of 1,6-bis((N-(tert-butyl)-1-methyl-1-(3-(1-pyrrolidinyl)-1H-inden-1-yl)silanamine))hexane (2.45 g, 3.6 mmole) in 50 mL of toluene was added over 15 minutes a solution of n-butyl lithium in hexanes (1.60 M, 9.42 mL, 15.0 mmol). Over the period of addition, the original red solution turns orange followed by formation of a yellow precipitate. After stirring for 14 hours, the yellow precipitate was collected by filtration and washed twice with 10 mL of toluene and then twice with 10 mL of hexanes. The dark yellow solid was dried in vacuo for 8 hours to leave 2.6 g (quantitive yield) of the desired product.

D) ($\mu$-((1,1'-(1,6-hexanediyl)bis(N-(1,1-dimethylethyl)-1-methyl-1-((1,2,3,3a,7a-$\eta$)-3-(1-pyrrolidinyl)-1H-inden-1-yl)silanaminato-$\kappa$N)(4-)))) tetrachlorodititanium To a precooled (–30° C.) suspension of $TiCl_3(THF)_3$ (1.42 g, 3.82 mmol) in 30 mL of THF was added a precooled (–30° C.) 30 mL THF solution of 1,6-bis((N-(tert-butyl)-1-methyl-1-(3-(1-pyrrolidinyl)-1H-inden-1-yl)silanamine)) hexane, tetralithium salt (1.35 g, 1.91 mmol). Immediately the color changed to very dark blue/green. After stirring at room temperature for 45 minutes, $PbCl_2$ (0.8 g, 2.879 mmol) was added. The color gradually changed to dark blue/purple as lead balls formed. After 1 hour, the volatiles were removed in vacuo and the product extracted into 25 mL of toluene, filtered and the volatiles removed in vacuo. The dark blue/purple residue was dried in vacuo for 4 hours and then triturated in hexanes (30 mL). The hexanes were removed in vacuo and 30 mL of hexanes was added followed by trituration again. The resulting purple/black suspension was filtered, the solid washed with hexanes and dried in vacuo overnight to leave 1.42 g (83 percent yield) of the desired product as a purple/black solid.

$^1H$ NMR ($C_6D_6$): 7.62 (br s, 4H), 7.08 (br s, 4H), 5.67 (m, 2H), 3.58 (br s, 4H), 3.22 (brs, 4H), 1.49 (brs, 36H), 1.8–0.50 (m, 23H), $^{13}C\{^1H\}$ ($C_6D_6$): 149.7 (m), 136.5, 135.5, 129.04, 128.9, 127.2, 126.4, 125.3, 106.77/106.29 (isomers), 92.3, 60.9, 50.6, 25.7, 24.3/24.0 (isomers), 19.7, 18.19, 14.34, 1.87/–0.54 (isomers).

EXAMPLE 2

(μ-((1,1'-(1,6-hexanediyl)bis(N-(1,1-dimethylethyl)-1-methyl-1-((1,2,3,3a,7a-η)-3-(1-pyrrolidinyl)-1H-inden-1-yl)silanaminato-κN)(4-))))tetramethyldititanium

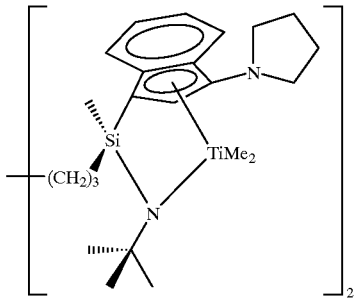

To a suspension of (μ-((1,1'-(1,6-hexanediyl)bis(N-(1,1-dimethylethyl)-1-methyl-1-((1,2,3,3a,7a-η)-3-(1-pyrrolidinyl)-1H-inden-1-yl)silanaminato-κN)(4-))))tetrachlorodititanium (0.189 g, 0.21 mmol) in 10 mL of diethyl ether was added a solution of MeLi (1.4 M/Et$_2$O, 0.59 mL, 0.82 mmol). Instantly the solution turned dark red. After stirring at room temperature for 1 hour, the volatiles were removed in vacuo and the product extracted into 20 mL of hexanes. The suspension was filtered and the brown filter cake washed until no appreciable red color appeared in the washing. The volatiles were removed from the red filtrate and the residue dried in vacuo for 1 hour. The residue was extracted into hexanes (15 mL) and filtered to remove trace amounts of fine particulates. The hexanes were removed from the filtrate in vacuo and the resulting red 'flaky' solid dried in vacuo overnight to leave 0.130 g (75 percent yield) of red solid.

$^1$H NMR (C$_6$D$_6$): 7.73 (m, 2H), 7.50 (m, 2H), 7.04 (m, 2H), 6.89 (m, 2H), 5.42 (m, 2H), 3.43 (m, 4H), 3.25 (m, 4H), 1.53 (sh m, 36H), 1.8–0.50 (m, 20H), 0.09 (br s, 6H). $^{13}$C{$^1$H} (C$_6$D$_6$): 144.16 (m), 133.99, 133.31, 125.60, 125.13, 124.73, 123.90, 104.642, 104.02, 83.90, 57.78, 54.34, 54.13, 50.63, 48.86, 34.91, 33.99, 33.86, 26.05, 24.73, 24.38, 20.84, 19.20, 2.86, 0.39.

EXAMPLE 3

(μ-((1,1'-(1,2-ethanediyl)bis(N-(1,1-dimethylethyl)-1-methyl-1-((1,2,3,3a,7a-η)-3-(1pyrrolidinyl)-1H-inden-1-yl)silanaminato-κN)(4-))))tetrachlorodititanium

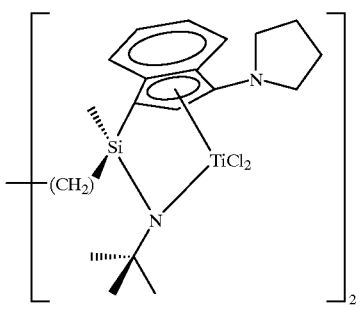

A) 1,1'-(1,2-ethanediyl)bis(1-chloro-N-(1,1-dimethylethyl)-1-methyl)silanamine To a −10° C. solution of and 1,6-bis(dichloromethylsilyl)ethane (5.00 g, 19.5 mmol) and triethylamine (6.0 mL, 43 mmol) in 50 mL of CH$_2$Cl$_2$ was added dropwise over 1 hour a solution of tert-butylamine (4.1 mL, 39.0 mmol) in 20 mL of CH$_2$Cl$_2$. The obtained white suspension was allowed to warm to room temperature. After stirring for 16 hours, most of the solvent was removed in vacuo and 75 mL of hexanes added. The resulting suspension was filtered and the volatiles removed from the filtrate in vacuo to leave 1,6-bis(N-(tert-butyl)-1-chloro-1-methylsilanamine)ethane (5.7 g, 97 percent yield) as a pale pink oily solid.

$^1$H NMR (C$_6$D$_6$): 1.12 (s, 18H), 1.03 (br s, 2H), 0.91 (m, 4H), 0.33/0.32. (two s, 6H, isomers). $^{13}$C{$^1$H} (C$_6$D$_6$): 50.36, 33.32, 32.95, 12.65/12. (two peaks/isomers), 2.39/2.13 (two peaks/isomers).

B) 1,1'-(1,2-ethanediyl)bis(N-(1,1-dimethylethyl)-1-methyl-1-(3-(1-pyrrolidinyl)-1H-inden-1-yl)-silanamine To a −30° C. solution of (1-(1-pyrrolidinyl)-1H-indenyl) lithium (1.705 g, 8.92 mmol) in 10 mL of THF was added a −30° C. solution of 1,6-bis(N-(tert-butyl)-1-chloro-1-methylsilanamine)ethane (1.47 g, 4.46 mmol) in 5 mL of THF. The reaction was allowed to warm to room temperature as it gradually darkened and changed to a deep-red/purple solution with slight green fluorescence. After 16 hrs at room temperature, the volatiles were removed in vacuo and then 50 mL of hexanes was added. The suspension was filtered and the hexanes removed from the filtrate in vacuo to leave 1,6-bis((N-(tert-butyl)-1-methyl-1-(3-(1-pyrrolidinyl)-1H-inden-1-yl)silanamine)ethane (2.7 g, 97% yield) as a red/purple oil.

$^1$H NMR (C$_6$D$_6$): 7.75–7.55 (m, 4H), 7.40–7.15 (m, 4H), 5.42 (m, 2H), 3.505 (m, 2H), 3.29 (br s, 8H), 1.65 (br s, 8H), 1.09 (set of several sharp peaks, 18H), 0.88 (m, 2H), 0.54 (m, 4H), 0.45–0.00 (m, 6H). $^{13}$C{$^1$H} (C$_6$D$_6$): 149.07, 147.03, 141.59, 124.58, 124.39, 123.98, 123.78, 120.92, 105.22, 50.86, 49.49, 42.80 (m), 34.13, 25.43, 11.0–8.0 (m), 0.0–(−3.0) (m).

C) 1,1'-(1,2-ethanediyl)bis(N-(1,1-dimethylethyl)-1-methyl-1-(3-(1-pyrrolidinyl)-1H-inden-1-yl)$^{-2}$, (deloc-1,2,3,3a,7a:1', 2',3',3'a,7'a)-silanamine, dilithium, dilithium salt To a stirred solution of 1,6-bis((N-(tert-butyl)-1-methyl-1-(3-(1-pyrrolidinyl)-1H-inden-1-yl)silanamine))ethane (2.7 g, 4.31 mmol) in 50 mL of toluene was added n-BuLi (11.3 ml, 1.6 M, 18.1 mmol) over fifteen minutes. The original red solution slowly turned to a orange-yellow suspension over one hour. After 16 hours, the yellow/orange suspension was filtered and washed with toluene until the washings became colorless (4×5 mL washes). The sample was then washed 3 times with 20 mL of hexanes and dried in vacuo for 5 hours to leave 2.60 g (93 percent yield) of 1,6-bis((N-(tert-butyl)-1-methyl-1-(3-(1-pyrrolidinyl)-1H-inden-1-yl)silanamine))ethane, tetralithium salt as a fine yellow powder.

D) (μ-((1,1'-(1,2-ethanediyl)bis(N-(1,1-dimethylethyl)-1-methyl-1-((1,2,3,3a,7a-η)-3-(1-pyrrolidinyl)-1H-inden-1-yl)silanaminato-κN)(4-))))tetrachlorodititanium To a precooled (−30° C.) suspension of TiCl$_3$(THF)$_3$ (1.27 g, 3.44 mmol) in 20 mL of THF was added a precooled (−30° C.) 20 mL THF solution of 1,6-bis((N-(tert-butyl)-1-methyl-1-(3-(1-pyrrolidinyl)-1H-inden-1-yl)silanamine)) ethane, tetralithium salt (1.12 g, 1.72 mmol). Immediately the color changed to very dark blue/green. After stirring at room temperature for 1 hour, PbCl$_2$ (0.67 g, 2.4 mmol)was added. The color gradually changed to dark blue/purple as lead particles formed. After 1 hour, the volatiles were removed in vacuo and the residue dried in vacuo for 1 hour. The product was extracted into 60 mL of toluene, filtered and the volatiles removed in vacuo. After drying the dark residue in vacuo for an hour, hexanes (20 mL) was added and the dark solid triturated. The volatiles were removed in vacuo, 20 mL of hexanes were added and the solid triturated again. The resulting purple/black suspension was filtered and the solid washed twice with 3 mL of hexanes and dried in vacuo overnight to leave 1.35 g (91 percent yield) of the desired product as a dark purple solid.

$^1$H NMR (C$_6$D$_6$): 7.80–7.55 (m, 4H), 7.30–6.70 (m, 4H), 5.75 (m, 2H), 3.75–3.00 (m, 4H), 1.45 (br s, 36H), 1.90–0.50 (m, 15H). $^{13}$C{$^1$H} (C$_6$D$_6$): 149.9 (m), 136.4, 135.5, 129.5, 129.3, 129.1, 127.4, 126.6, 126.4, 126.1, 106.1 (m), 92.4, 61.1, 50.7, 33.3, 25.9, 15–9 (m), 0.92/0.81/−1.19 (isomers).

EXAMPLE 4

(μ-((1,1'-(1,2-ethanediyl)bis(N-(1,1-dimethylethyl)-1-methyl-1-((1,2,3,3a,7a-η)-3-(1-pyrrolidinyl)-1H-inden-1-yl)silanaminato-κN)(4-))))tetramethyldititanium

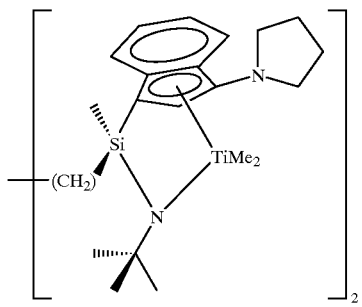

To a suspension of (μ-((1,1'-(1,2-ethanediyl)bis(N-(1,1-dimethylethyl)-1-methyl-1-((1,2,3,3a,7a-η)-3-(1-pyrrolidinyl)-1H-inden-1-yl)silanaminato-κN)(4-)))) tetrachlorodititanium (0.430 g, 0.50 mmol) in 25 mL of diethyl ether was added a solution of MeLi (1.4 M/Et$_2$O, 1.43 mL, 2.00 mmol). Instantly the solution turned dark red. After stirring at room temperature for 1 hour, the volatiles were removed in vacuo and the sample dried in vacuo for 1 hour. The product was extracted into 50 mL of hexanes, the suspension filtered and the brown filter cake washed until no appreciable red color appeared in the washing. The volatiles were removed from the red filtrate and the residue dried in vacuo for 2 hours. The residue was extracted again into hexanes (15 mL) and filtered to remove trace amounts of an insoluble brown residue. The hexanes were removed from the filtrate in vacuo and the resulting red solid dried in vacuo overnight to leave 0.280 g (67 percent yield) of red solid.

$^1$H NMR (C$_6$D$_6$): 7.85–7.45 (m, 4H), 7.10–6.65 (m, 4H), 5.56 (m, 2H), 3.46 (br s, 4H), 3.28 (br m, 4H), 1.55 (sh m, 36H), 1.8–0.50 (m, 12H), 0.09 (m, 6H). $^{13}$C{$^1$H} (C$_6$D$_6$): 144.2 (m), 134.1, 133.8, 126.0–124.0 (m), 104.6 (m), 83.85 (m), 57.89 (m), 54.5 (m), 50.52 (m), 51.0–49.0 (m), 34.99, 26.09, 15.0–10.0 (m), 2.0 (m), −0.40 (m).

EXAMPLE 5

(μ-((1,1'-(1,6-hexanediyl)bis(N-(1,1-dimethylethyl)-1-methyl-1-((1,2,3,4,5-η)-2,3,4,5-tetramethyl-2,4-cyclopentadien-1-yl)silanaminato-κN)(4-))))tetrakis(phenylmethyl)di-titanium

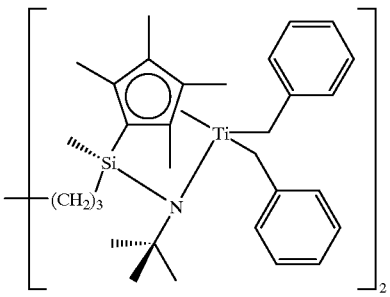

A) 1,6-hexanediylbis(chloromethyl(2,3,4,5-tetramethyl-2,4-cyclopentadien-1-yl)silane To a −10° C. solution of 1,6-bis(dichloromethylsilyl)hexane in 50 mL of THF was added dropwise over 1 hour a 30 mL THF solution of (2,3,4,5-tetramethycyclopentadienyl)magnesium-bromide.(THF)$_x$ (1.75 g, 5.49 mmol, 319 g/mol effective MW). The nearly colorless reaction was allowed to slowly warm to room temperature. After stirring overnight, the volatiles were removed in vacuo. The product was extracted into 75 mL of hexanes, filtered and the filter cake washed several times with hexanes. The volatiles were removed from the filtrate in vacuo to leave 1.25 g (94 percent yield) of 1,6-bis(1-(1,2,3,4-tetramethylcyclopentadienyl)-1-chloro-1-methylsilyl)hexane as a off-white waxy solid.

$^1$H NMR (C$_6$D$_6$): 2.99 (br s, 2H), 1.98 (overlapping s, 12H), 1.754 (s, 12H), 1.50–1.10 (m, 8H), 0.80–0.50 (m, 4H), 0.19(s,6H). $^{13}$C{$^1$H} (C$_6$D$_6$):137.87, 131.65, 55.98, 33.12, 23.64, 16.74,14.67, 11.51, −0.64.

B) 1,1'-(1,6-hexanediyl)bis(N-(1,1-dimethylethyl)-1-methyl-1-(2,3,4,5-tetramethyl-2,4-cyclopentadien-1-yl)silanamine To a solution of triethylamine (0.9 mL, 6.46 mmol) and 1,6-bis(1-(1,2,3,4-tetramethylcyclopentadienyl)-1-chloro-1-methylsilyl)hexane (1.25 g, 2.58 mmol) in 30 mL of CH$_2$Cl$_2$ was added tert-butylamine (0.6 mL, 5.69 mmol) all at once. The solution became cloudy as white precipitate formed. After stirring at room temperature for 2 hours, the volatiles were removed in vacuo and hexanes were added (30 mL). The hexanes extract was filtered and the filter cake washed twice with hexanes. The volatiles were removed from the filtrate in vacuo to leave 1.4 g (97percent yield) of 1,6-bis (N-(tert-butyl)-1-(1,2,3,4-tetramethyl-cyclopentadienyl)-1-methylsilanamine)hexane as a pale-yellow, viscous oil.

$^1$H NMR (C$_6$D$_6$): 2.89 (br s, 2H), 2.15–1.70 (m, 265H), 1.41 (br s, 8H), 1.12 (s, 18H), 0.58/0.40 (m, 4H), 0.24 (s, 6H). $^{13}$C{$^1$H} (C$_6$D$_6$): 135.50, 133.47, 133.13, 56.37, 49.49, 34.03, 33.88, 24.61, 23.93, 17.12,15.28/15.18, 11.61, 0.50.

C) (μ-((1,1'-(1,6-hexanediyl)bis(N-(1,1-dimethylethyl)-1-methyl-1-((1,2,3,4,5-η)-2,3,4,5-tetramethyl-2,4-cyclopentadien-1-yl)silanaminato-κN)(4-))))tetrakis(phenylmethyl)di-titanium A Schlenk flask was charged with a hexanes solution (80 mL) of tetra(benzyl)titanium (1.433 g, 3.47 mmol) and 1,6-bis(N-(tert-butyl)-1-(tetramethylcyclopentadienyl)-1-methylsilanamine)hexane (0.88 mg, 1.58 mmol). The reaction was heated to 60° C. for 22 hours. The reaction was taken into the glovebox and heated to reflux for 4 hours. The volatiles were removed in vacuo, the residue extracted with hexanes (75 mL), filtered and the volatiles removed in vacuo. The residue was again extracted into hexanes (50 mL), filtered, and the filtrate concentrated to about 10 mL. After cooling the solution at −30° C. overnight, the mother liquor was filtered and the oily dark solid washed twice with 5 mL of hexanes. The volatiles were removed from the filtrate in vacuo to leave 1.2 g (75 percent yield) of the desired product as an oily gold-brown solid.

$^1$H NMR (C$_6$D$_6$): 7.13 (m, 8H), 6.85 (m, 12H), 3.0–0.0 (several overlapping multiplets with distinct peaks at around 1.75, 1.45 and 0.5 ppm). $^{13}$C{$^1$H} (C$_6$D$_6$): 150.35, 134.92, 134.32, 131.85 (m), 128.35, 127.15 (br s), 122.92, 122.34, 83.10, 82.06, 84–80 (underlying mult.), 60.18, 38.5, 36.75, 34.49, 33.92, 16.0–11.0 (m), 3.45.

EXAMPLE 6

(μ-((1,1'-(1,2-ethanediyl)bis(N-(1,1-dimethylethyl)-1-methyl-1-((1,2,3,4,5-η)-2,3,4,5-tetramethyl-2,4-cyclopentadien-1-yl)silanaminato-κN)(4-))))tetrakis(phenylmethyl)di-titanium

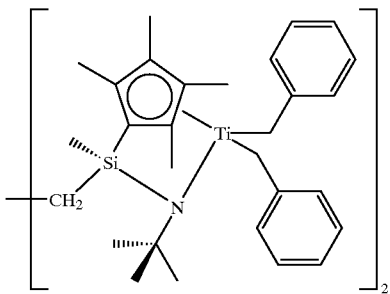

A) 1,2-ethanediylbis(chloromethyl(2,3,4,5-tetramethyl-2,4-cyclopentadien-1-yl)silane To a 0° C. solution of 1,6-bis(dichloromethylsilyl)ethane (5.73 9, 22.4 mmol) in 100 mL of THF was added dropwise over 1.5 hour a 300 mL THF solution of (2,3,4,5-tetramethylcyclopentadienyl)magnesiumchlorides(THF)) (11.06 g, 44.8 mmol, 247 g/mol effective MW). The reaction was allowed to slowly warm to room temperature overnight. After 17 hours, the volatiles were removed in vacuo and the resulting off white solid dried in vacuo for an additional hour. To the solid was added 150 mL of hexanes and the suspension vigorously stirred for 10 minutes. The suspension was filtered and the volatiles removed in vacuo from the pale yellow filtrate. After thorough drying, 9.41 g (98 percent yield) of the desired product was obtained as an off-white solid.

$^1$H NMR (C$_6$D$_6$): 2.97 (br s, 2H), 1.99 (s, 6H), 1.92 (s, 6H), 1.74 (s, 12H), 0.9–0.5 (m, 4H), 0.15 (s, 6H). $^{13}$C{$^1$H} (C$_6$D$_6$): 138.02, 131.58 (br), 55.67, 14.67, 11.52, 9.13,−1.18.

B) 1,1'-(1,6-ethanediyl)bis(N-(1,1-dimethylethyl)-1-methyl-1-(2,3,4,5-tetramethyl-2,4-cyclopentadien-1-yl)silanamine To a solution of triethylamine (7.7 mL, 55 mmol) and 1,2-ethanediylbis(chloromethyl-(2,3,4,5-tetramethyl-2,4-cyclopentadien-1-yl)-silane (9.4 g, 21.98 mmol) in 80 mL of CH$_2$Cl$_2$ was added tert-butylamine (5.1 mL, 48 mmol) all at once. A white suspension quickly formed. After stirring for three hours, the volatiles were removed in vacuo and the product into hexanes (120 mL). The suspension was filtered and washed twice with 10 mL of hexanes. The hexanes were remove in vacuo to leave 10.33 g (100 percent yield) of 1,6-bis(N-(tert-butyl)-1-(1,2,3,4-tetramethyl-cyclopentadienyl)-1-methylsilanamine)ethane as a pale-yellow, viscous oil.

$^1$H NMR (C$_6$D$_6$): 2.90/2.82 (two s, 2H, isomers), 2.10–1.70 (m, 26H), 1.13/1.10 (two s, 18H, isomers), 0.46 (m, 4H), 0.30–0.15 (m, 6H). $^{13}$C{$^1$H} (C$_6$D$_6$): 135.4 (m), 133.67, 133.22, 56.14 (m), 49.37, 33.95, 15.05 (m), 11.46, 9.01 (m), −0.20 (m).

C) (μ-((1,1'-(1,2-ethanediyl)bis(N-(1,1-dimethylethyl)-1-methyl-1-((1,2,3,4,5-η)-2,3,4,5-tetramethyl-2,4-cyclopentadien-1-yl)silanaminato-κN)(4-)))tetrakis(phenylmethyl)dititanium A Schlenk flask was charged with a hexanes solution (90 mL) of tetra(benzyl)titanium (1.97 g, 4.78 mmol) and 1,6-bis(N-(tert-butyl)-1-(Me$_4$Cp)-1-methylsilanamine)ethane (1.022 g, 2.17 mmol). The reaction was heated to 60° C. for 19 hours and the resulting dark yellow/brown solution was then heated to reflux for an additional four hours. The volatiles were removed in vacuo and the product extracted into hexanes (100 mL). The suspension was filtered to remove some black solid and the volatiles were removed from the filtrate. The residue was dried in vacuo for one hour and then extracted with hexanes again (70 mL). The suspension was filtered and the volatiles removed from the filtrate. The residue was again extracted with hexanes (50 mL), filtered and the filtrate concentrated to about 20 mL. The dark solution was cooled at −30° C. overnight. The solution was decanted away from the black oily residue and the residue washed twice with 5 mL of hexanes. The hexanes filtrate was concentrated to 5 mL and cooled at −30° C. overnight. The solution was filtered and the small amount of black insoluble residue was washed with hexanes. The volatiles were removed from the hexanes filtrate in vacuo and the solid dried in vacuo for 5 hours to leave 1.25 g (62 percent yield) of desired complex as a dark gold-brown solid.

$^1$H NMR (C$_6$D$_6$): 7.13 (m, 8H), 6.85 (m, 12H), 3.0–0.0 (several overlapping multiplets with distinct peaks at around 1.75, 1.45 and 0.5 ppm). $^{13}$C{$^1$H} (C$_6$D$_6$): 150.35, 134.92, 134.32, 131.85 (m), 128.35, 127.15 (brs), 122.92, 122.34, 83.10, 82.06, 84–80 (underlying multiplets), 60.18, 38.5, 36.75, 34.49, 33.92, 16.0–11.0 (m), 3.45.

EXAMPLE 7 bis(1,1'-(η$^4$-1,3-butadiene-1,4-diyl)bis(benzene))(L-(1,6-hexanediylbis((methylsilylidyne)bis((1,2,3,3a,7a-η)-2-methyl-4-phenyl-1H-inden-1-ylidene)))) dizirconium

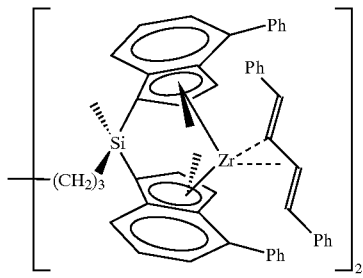

A) Lithium 2-methyl-4-phenylindenide

To a solution of 2-methyl-4-phenylindene (10.03 g, 49.3 mmol) in 200 mL of hexanes was added dropwise over 10 minutes 32 mL of 1.6M n-BuLi. The resulting yellow suspension was stirred for 17 hours. The suspension was filtered and the solid washed twice with 5 mL of hexane. The light yellow solid was dried in vacuo for 2 hours to leave 9.21 g (89 percent yield) of lithium 2-methyl-4-phenylindenide. A second crop (0.61 g) was obtained by concentrating the filtrate to about 80 mL and filtering after 4 hours at room temperature. Overall yield was 9.82 g, 95 percent.

B) 1.6-hexanediylbis(methylbis(2-methyl-4-phenyl-1H-inden-1-yl)-silane

A solution of 1,6-bis(dichloromethylsilyl)hexane (1.78 g, 5.69 mmol) in 20 mL of toluene was added dropwise over 30 minutes to a solution of lithium 2-methyl-4-phenylindenide (5.00 g, 23.9 mmol) in 60 mL of THF. The cloudy orange solution was left to stir at room temperature for 20 hours and then quenched by slow addition of water (80 mL). Most of the THF was removed by rotary evaporation and the product extracted into diethyl ether (120 mL). The organic/aqueous layers were separated and the aqueous layer washed twice with 50 mL of diethyl ether. The organic extracts were combined, dried over MgSO$_4$, filtered and most of the volatiles removed in vacuo. The reaction residue was dissolved in enough toluene to make about 25 mL of a viscous solution. The reaction mixture was subsequently chromatographed on silica (35 cm×5 cm column) initially eluting with hexanes followed by 4:1 hexanes:CH$_2$Cl$_2$ to remove excess 2-methyl-4-phenylindene (Rf=0.62 (silica, 2:1 hexanes:dichloromethane). Further elution with 4:1 hexanes:CH$_2$Cl$_2$ gave one fraction of the desired product 1,6-bis[methylsilyl-bis(2-methyl-4-phenyl-indenyl)hexane (Rf≅0.38 silica, 2:1 hexanes:dichloromethane) which was isolated by removal of volatiles in vacuo to leave 1.53 g (27%) of pale yellow solid. Further elution with 3:1 hexanes:CH$_2$Cl$_2$ led to isolation of a second fraction which has a much broader elution bandwidth (Rf≅0.35–0.10). Removal of volatiles in vacuo from the sample gave 1.89 g (34 percent) of pale yellow solid. Overall yield was 3.42 g (61 percent).

$^1$H NMR (CDCl$_3$): 7.70–6.9 (m, 32H), 6.74 (m, 4H), 4.0–3.5 (m, 4H), 2.4–1.9 (m, 12H), 1.6–0.4 (m, 12H), 0.45–(−0.2) (m, 6H). $^{13}$C{$^1$H} (CDCl$_3$): 158.2, 150.9, 148.2 (m), 145.9, 143.1 (m), 141.6 (m), 140.55, 137.6, 134.31, 130–120 (several multiplets.), 77.1 (m), 48.9, 47.3 (m), 33.5, 24.1, 18.1 (m), 15.1 (m), 13.2 (m), 12.4 (m), −5.4 (m).

B) 1,6-hexanediylbis(methylbis(2-methyl-4-phenyl-1H-inden-1-yl)-silane, ion(4-), tetralithium To a 20 mL toluene solution of 1,6-bis[methylsilyl-bis(2-methyl-4-phenyl-indenyl)hexane (1.01 g, 1.04 mmol) was added n-butyl lithium over 10 minutes (2.7 mL, 1.6 M in hexanes, 4.29 mmol). After 20–30 minutes, a yellow precipitate began to form. After stirring for 18 hours at room temperature, the yellow-orange suspension was filtered and washed twice with 6 mL of toluene then twice with 5 mL of hexane. The sample was dried in vacuo for 5 hours until the weight of sample stabilized to leave 0.91 g (89 percent yield) of tetralithium 1,6-bis[methylsilyl-bis(2-methyl-4-phenyl-indenylide)hexane as a yellow powder.

C) bis(1,1'-(n$^4$-1,3-butadiene-1,4-diyl)bis(benzene))(μ-(1,6-hexanediylbis((methylsilylidyne)bis((1,2,3,3a,7-η)-2-methyl-4-phenyl-1H-inden-1-ylidene)))) dizirconium To a −30° C. suspension of tetralithium 1,6-bis[methylsilyl-bis(2-methyl-4-phenyl-indenylide)hexane (0.300 mg, 0.30 mmol) in 5 mL of toluene was added a −30° C. solution of bis(triethylphosphine)(1,4-diphenylbutadiene)zirconium dichloride (0.432 g, 0.60 mmol) in 10 mL of toluene. The reaction was allowed to slowly warm to room temperature as the dark purple/black solution turned red. After stirring overnight, the solution was filtered and the volatiles removed in vacuo. The reaction residue was dissolved in 40 mL of toluene and added dropwise to 60 mL of hexanes. An additional 50 mL of 3:2 hexanes:toluene solvent mixture was added and the resulting orange/brown precipitate filtered and washed extensively with hexanes (3×30 mL). The volatiles were removed from the dark red filtrate and the oily red solid triturated with 10 mL of hexanes and the volatiles removed in vacuo. The trituration was repeated once more with 10 mL of hexanes and the obtained solid was filtered and washed with 5 mL of hexanes. The deep red solid was dried in vacuo overnight to leave 0.306 g (65 percent) of the desired product.

$^1$H NMR (CDCl$_3$): 8.0–7.6 (m, 4H), 7.6–6.6 (m, 52H), 5.6 (br s, 4H), 3.4 (m, 4H), 2.1–0.5 (m, 30H). $^{13}$C{$^1$H} (C$_6$D$_6$): 158.2, 150.9, 148.2 (m), 145.9, 143.1 (m), 141.6 (m), 140.55, 137.6, 134.31, 130–120 (several multiplets.), 77.1 (m), 48.9, 47.3 (m), 33.5, 24.1, 18.1 (m), 15.1 (m), 13.2 (m), 12.4 (m), −5.4 (m).

Polymerization

A two liter reactor is charged with 750 g of Isopar E and 120 g of octene-1 comonomer. Hydrogen is added as a molecular weight control agent by differential pressure expansion from a 75 ml additional tank from 300 psig (2070 Kpa) to 275 psig (1890 Kpa). The reactor is heated to the polymerization temperature of 140° C. and saturated with ethylene at 500 psig (3450 Kpa). The appropriate amount of catalyst and cocatalyst (trispentafluorophenyl)borane as 0.005 M solutions in toluene (approximately 4 μmole complex based on metal content) were premixed in a glovebox to give a 1:1 molar ratio of catalyst and cocatalyst, and transferred to a catalyst addition tank and injected into the reactor. The polymerization conditions were maintained for 10 minutes with ethylene on demand. The resulting solution was removed from the reactor into a nitrogen purged collection vessel containing 100 ml of isopropyl alcohol and 20 ml of a 10 weight percent toluene solution of hindered phenol antioxidant (Irganox™ 1010 from Ciba Geigy Corporation) and phosphorus stabilizer (Irgafos 168). Polymers formed are dried in a programmed vacuum oven with a maximum temperature of 120° C. and a 20 hours heating cycle. Results are shown in Table 1.

TABLE 1

| Run | complex | Efficiency[1] | MI[2] | density[3] | Mw/Mn |
|-----|---------|---------------|-------|------------|-------|
| 1 | Ex. 2 | 0.6 | <0.1 | 0.911 | 294,000/106,000 |
| 2 | Ex. 4 | 0.3 | 0.1 | 0.911 | 299,000/138,000 |
| 3 | Ex. 6 | 0.4 | 1.7 | 0.900 | 108,000/42,300 |
| 4 | Ex. 5 | 0.5 | 1.9 | 0.901 | 106,000/50,600 |
| 5 | Ex. 7 | 0.8 | 9.0 | 0.892 | 69,900/28,700 |
| 6* | TTiD[4] | 0.7 | 12.1 | 0.904 | 61,900/28,200 |
| 7* | BZrD[5] | 1.8 | 10.7 | 0.886 | 67,300/29,300 |

*not an example of the invention
[1]efficiency, g polymer/μg metal
[2]melt index, dg/min, measured by micromelt indexer
[3](g/cm³)
[4]1,2-ethanebis(2-methyl-4-phenylinden-1-yl)zirconium (II) 1,4-diphenyl-1-3- butadiene
[5](t-butylamido)dimethyl(tetramethylcyclopentadienyl)silanetitanium (II) 1,3-pentadiene

What is claimed is:

1. A dinuclear metal complexes corresponding to the formula:

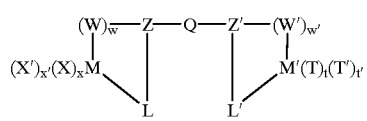

(I)

wherein:

M and M' are independently Group 3, 4, 5, 6, or Lanthanide metals;

L, L', W, and W', independently, are divalent groups having up to 50 nonhydrogen atoms and containing an aromatic π-system through which the group is bound to M, said L and W also being bound to Z, and said L' and W' also being bound to Z';

Z and Z' independently are trivalent moieties comprising boron or a member of Group 14 of the Periodic Table of the Elements, and optionally also comprising nitrogen, phosphorus, sulfur or oxygen, said Z and Z' having up to 20 atoms not counting hydrogen;

X and T independently each occurrence are anionic ligand groups having up to 40 atoms exclusive of the class of ligands containing an aromatic π-system through which the group is bound to M or M', or optionally two X groups or two T groups together form a $C_{4-40}$ conjugated or nonconjugated diene optionally substituted with one or more hydrocarbyl, silyl, halocarbyl, or halohydrocarbyl groups;

X' and T' independently each occurrence are neutral ligating compound having up to 20 atoms other than neutral diene compounds;

Q is a divalent anionic ligand group bound to both Z and Z', said Q having up to 20 nonhydrogen atoms;

w and w' are independently 0 or 1;

x and t are independently integers from 0 to 3, selected to provide charge balance; and x' and t' are independently numbers from 0 to 3.

2. A dinuclear metal coordination complex according to claim 1 corresponding to the formula:

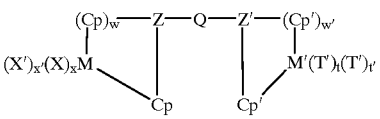

(II)

wherein

Z, Z', M, M', X, X', T, T', w, w', x, x', t, and t' are as defined in claim 1;

Cp and Cp', independently are cyclic $C_5R'_4$ groups bound to Z or Z' respectively and bound to M or M' respectively by means of delocalized π-electrons, wherein R', independently each occurrence, is hydrogen, hydrocarbyl, silyl, halo, fluorohydrocarbyl, hydrocarbyloxy, hydrocarbylsiloxy, N,N-di(hydrocarbylsilyl)amino, N-hydrocarbyl-N-silylamino, N,N-di(hydrocarbyl)amino, hydrocarbyleneamino, di(hydrocarbyl)phosphino, hydrocarbylsulfido; or hydrocarbyloxy-substituted hydrocarbyl, said R' having up to 20 nonhydrogen atoms, and optionally, two such R' substituents may be joined together thereby causing Cp or Cp' to have a fused ring structure; and Q is a linear or cyclic hydrocarbylene, or silane group or a nitrogen, oxygen, or halo substituted derivative thereof, said Q having up to 20 atoms, not counting hydrogen.

3. A metal complex according to claim 1, corresponding to the formula:

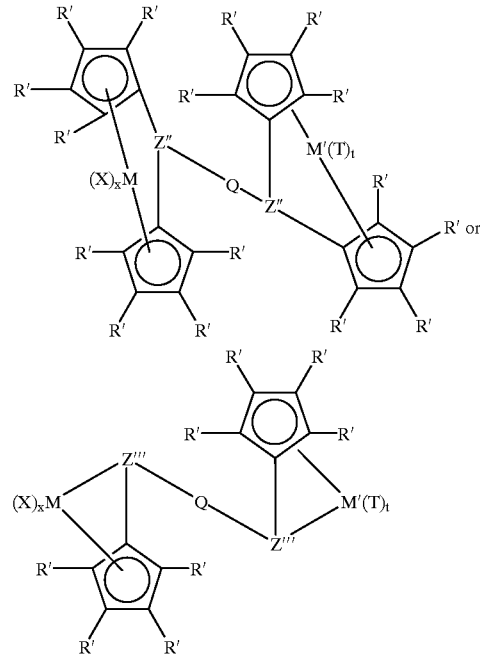

wherein:

R' each occurrence is hydrogen, hydrocarbyl, silyl, germyl, halo, cyano, halohydrocarbyl, hydrocarbyloxy, hydrocarbylsiloxy, di(hydrocarbylsilyl)amino, hydrocarbylsilylamino, di(hydrocarbyl)amino, hydrocarbyleneamino, di(hydrocarbyl)phosphino, hydrocarbylsulfido; or hydrocarbyloxy-substituted hydrocarbyl, said R' having up to 20 nonhydrogen atoms, and optionally, two R' groups together form a divalent derivative thereof connected to adjacent positions of the cyclopentadienyl ring thereby forming a fused ring structure, or R' in one occurrence per cyclopentadienyl system is a covalent bond to Q;

Z" independently each occurrence is a trivalent group selected from SiR*, CR*, SiR*SiR*$_2$, CR*CR*$_2$, CR*SiR*$_2$, CR*$_2$SiR*, or GeR*; wherein R* each occurrence is independently hydrogen, hydrocarbyl, silyl, halogenated alkyl, or halogenated aryl, said R* having up to 12 non-hydrogen atoms;

Z'" independently each occurrence is —Z"Y'—, wherein:

Y' is —O—, —S—, —NR"—, —PR"—, —OR", or —NR"$_2$ (and with respect to —OR" and —NR"$_2$, one bond is a dative bond through the available electron pair), wherein R" is hydrogen, hydrocarbyl, silyl, or silylhydrocarbyl of up to 20 atoms not counting hydrogen;

M and M' independently are Ti, Zr or Hf;

X and T, independently are halide or hydrocarbyl or two X groups together or two T groups together are a conjugated diene group, said X and T groups having up to 20 atoms not counting hydrogen; and Q is a linear or cyclic hydrocarbylene group, silane group, or silyl substituted hydrocarbylene group, or a nitrogen, oxygen, or halo substituted derivative thereof, said Q having up to 20 atoms not counting hydrogen.

4. A metal complex according to claim 3, wherein R' independently each occurrence is hydrogen, hydrocarbyl, silyl, fluorophenyl, hydrocarbyloxy, N,N-di(hydrocarbyl) amino, hydrocarbyleneamino, or hydrocarbyloxy-substituted hydrocarbyl, said R' having up to 20 non-hydrogen atoms, or two adjacent R' groups are joined together forming part of a fused ring system.

5. A metal complex according to claim 4 wherein R' independently each occurrence is hydrogen, methyl, ethyl, propyl, butyl, pentyl, hexyl, (including where appropriate all isomers), cyclopentyl, cyclohexyl, norbornyl, benzyl, phenyl, N,N-di(methyl)amino, pyrrolyl, pyrrolidinyl, or two R' groups are linked together, the entire C$_5$R'$_4$ group thereby forming an indenyl, tetrahydroindenyl, fluorenyl, tetrahydrofluorenyl, indacenyl, or octahydrofluorenyl group, or a C$_{1-6}$ hydrocarbyl-, N,N-di(methyl)amino-, pyrrolyl-, or pyrrolidinyl-substituted derivative thereof.

6. A dinuclear metal complex according to claim 5, corresponding to the formula:

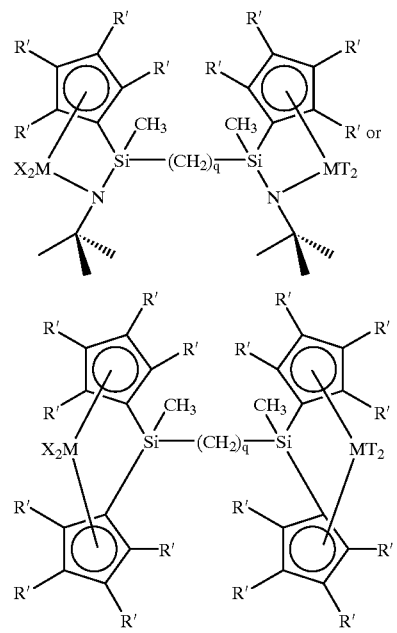

wherein

M is titanium or zirconium;

q is an integer from 2 to 10;

R' is methyl or all R' groups collectively with the cyclopentadienyl group form a 2,3,4,6-tetramethylinden-1-yl, 3-(N-pyrrolidinyl)inden-1-yl, or a 2-methyl-4-phenylinden-1-yl group; and X and T, independently each occurrence, are chloride, methyl, benzyl or 2 X groups or two T groups together form a 1,4-diphenyl-1,3-butadiene or 1,3-pentadiene group.

7. In a process for the coordination polymerization of polymerizable monomers the improvement wherein the catalyst comprises a dinuclear complex according to any one of claims 1 to 6 and an activating cocatalyst.

* * * * *